US012766311B2

(12) United States Patent
Bryson et al.

(10) Patent No.: US 12,766,311 B2
(45) Date of Patent: Oct. 20, 2026

(54) INFLOW / OUTFLOW CANNULA ANCHORS

(71) Applicant: W. L. Gore & Associates, Inc., Newark, DE (US)

(72) Inventors: Scott M. Bryson, Newark, DE (US); Daniel Dominguez, Anthem, AZ (US); James L. Goepfrich, Flagstaff, AZ (US); Edward E. Shaw, Flagstaff, AZ (US)

(73) Assignee: W. L. Gore & Associates. Inc., Newark, DE (US)

( * ) Notice: Subject to any disclaimer, the term of this patent is extended or adjusted under 35 U.S.C. 154(b) by 154 days.

(21) Appl. No.: 18/699,031

(22) PCT Filed: Oct. 5, 2022

(86) PCT No.: PCT/US2022/045771
§ 371 (c)(1),
(2) Date: Apr. 5, 2024

(87) PCT Pub. No.: WO2023/059711
PCT Pub. Date: Apr. 13, 2023

(65) Prior Publication Data

US 2024/0408379 A1 Dec. 12, 2024

Related U.S. Application Data

(60) Provisional application No. 63/253,402, filed on Oct. 7, 2021.

(51) Int. Cl.
*A61M 60/90* (2021.01)

(52) U.S. Cl.
CPC ......... *A61M 60/90* (2021.01); *A61M 2205/04* (2013.01); *A61M 2209/088* (2013.01); *A61M 2210/125* (2013.01)

(58) Field of Classification Search
CPC ..................................................... A61M 60/90
(Continued)

(56) References Cited

U.S. PATENT DOCUMENTS 4,877,661 A 10/1989 House et al.
5,098,369 A 3/1992 Heilman et al.
(Continued)

FOREIGN PATENT DOCUMENTS

CN 103228300 A 7/2013
CN 105307700 A 2/2016
(Continued)

OTHER PUBLICATIONS

International Preliminary Report on Patentability received for PCT Patent Application No. PCT/US2021/016532, mailed on Aug. 18, 2022, 9 pages.

(Continued)

*Primary Examiner* — Nicole F Johnson

(57) ABSTRACT

Various aspects of the present disclosure are directed toward apparatuses, systems, and methods that may include an inflow or outflow cannula apparatus. A support structure of the cannula may include an elongate element having a rectangular cross-section, the elongate element being coupled to the exterior surface of a conduit of the cannula by a second graft component. A cannula may include a first stent element configured to facilitate folding of a first anchor portion toward an exterior surface of the conduit and adjacent a second stent element and the second stent element may be configured to facilitate folding of a second anchor portion toward the exterior surface of the conduit and adjacent the first stent element in a delivery configuration.

27 Claims, 11 Drawing Sheets

(58) Field of Classification Search
USPC .......................................................... 600/16
See application file for complete search history.

(56) References Cited

U.S. PATENT DOCUMENTS

| | | | | |
|---|---|---|---|---|
| 5,300,107 | A | 4/1994 | Stokes et al. | |
| 5,613,935 | A | 3/1997 | Jarvik | |
| 5,626,605 | A | 5/1997 | Irie et al. | |
| 5,628,782 | A | 5/1997 | Myers et al. | |
| 5,843,171 | A | 12/1998 | Campbell et al. | |
| 5,964,694 | A | 10/1999 | Sieb et al. | |
| 6,315,792 | B1 | 11/2001 | Armstrong et al. | |
| 6,400,991 | B1 | 6/2002 | Kung | |
| 6,461,665 | B1 | 10/2002 | Scholander | |
| 6,936,058 | B2 | 8/2005 | Forde et al. | |
| 6,994,666 | B2 | 2/2006 | Shannon et al. | |
| 7,686,758 | B2 | 3/2010 | Nose et al. | |
| 8,398,694 | B2 | 3/2013 | Forde et al. | |
| 9,211,367 | B2 | 12/2015 | Farnan et al. | |
| 9,399,085 | B2 | 7/2016 | Cleek et al. | |
| 10,849,653 | B2 | 12/2020 | Tao et al. | |
| 12,121,713 | B2 * | 10/2024 | Calomeni | A61M 60/13 |
| 2004/0153112 | A1 | 8/2004 | Nissenbaum et al. | |
| 2004/0193004 | A1 | 9/2004 | Tsubouchi et al. | |
| 2005/0065589 | A1 | 3/2005 | Schneider et al. | |
| 2006/0052814 | A1 | 3/2006 | Sater | |
| 2006/0184088 | A1 | 8/2006 | Van Bibber et al. | |
| 2010/0249490 | A1 | 9/2010 | Farnan | |
| 2011/0196190 | A1 | 8/2011 | Farnan et al. | |
| 2012/0041375 | A1 | 2/2012 | Magana | |
| 2012/0059213 | A1 | 3/2012 | Spence | |
| 2013/0172661 | A1 | 7/2013 | Farnan et al. | |
| 2013/0338426 | A1 | 12/2013 | Marseille et al. | |
| 2014/0107399 | A1 | 4/2014 | Spence | |
| 2014/0200550 | A1 | 7/2014 | Farnan et al. | |
| 2014/0275865 | A1 | 9/2014 | Tammam et al. | |
| 2014/0371676 | A1 | 12/2014 | Leeflang et al. | |
| 2015/0223839 | A1 | 8/2015 | Spence et al. | |
| 2015/0290370 | A1 | 10/2015 | Crunkleton et al. | |
| 2017/0119943 | A1 | 5/2017 | Farnan | |
| 2017/0181751 | A1 | 6/2017 | Larsen et al. | |
| 2017/0197019 | A1 * | 7/2017 | Tuseth | A61M 60/122 |
| 2018/0133378 | A1 | 5/2018 | Askem et al. | |
| 2018/0214619 | A1 | 8/2018 | Cook | |
| 2019/0160212 | A1 | 5/2019 | Arslan et al. | |
| 2023/0338727 | A1 | 10/2023 | Alston, Jr. et al. | |
| 2024/0408378 | A1 | 12/2024 | Bryson et al. | |
| 2025/0135160 | A1 | 5/2025 | Alston et al. | |

FOREIGN PATENT DOCUMENTS

| | | | |
|---|---|---|---|
| EP | 0732087 | A1 | 9/1996 |
| EP | 2233165 | A2 | 9/2010 |
| EP | 2233169 | A1 | 9/2010 |
| EP | 2233165 | A3 | 12/2010 |
| FR | 1501024 | A | 11/1967 |
| JP | 2004-298623 | A | 10/2004 |
| JP | 2010-533550 | A | 10/2010 |
| WO | 2021/101622 | A1 | 5/2021 |

OTHER PUBLICATIONS

International Preliminary Report on Patentability received for PCT Patent Application No. PCT/US2022/045771, mailed on Apr. 18, 2024, 13 pages.
International Preliminary Report on Patentability received for PCT Patent Application No. PCT/US2022/045773, mailed on Apr. 18, 2024, 13 pages.
International Preliminary Report on Patentability received for PCT Patent Application No. PCT/US22/045886, mailed on Apr. 18, 2024, 11 pages.
International Search Report and Written Opinion received for PCT Patent Application No. PCT/US2021/016532, mailed on Oct. 22, 2021, 12 pages.
International Search Report and Written Opinion received for PCT Patent Application No. PCT/US2022/045771, mailed on May 9, 2023, 19 pages.
International Search Report and Written Opinion received for PCT Patent Application No. PCT/US2022/045886, mailed on May 31, 2023, 17 pages.
International Search Report and Written Opinion received for PCT Patent Application No. PCT/US2022/045773, mailed on May 4, 2023, 20 pages.
Invitation to Pay Additional Fees received for PCT Patent Application No. PCT/US2022/045773, mailed on Jan. 24, 2023, 12 pages.
Invitation to Pay Additional Fees received for PCT Patent Application No. PCT/US2022/045771, mailed on Jan. 30, 2023, 9 pages.
Invitation to Pay Additional Fees received for PCT Patent Application No. PCT/US2022/045886, mailed on Feb. 16, 2023, 8 pages.
Yi, Geng-Hua, "Safety and feasibility of percutaneous delivery of a novel circulatory assist device (CircuLite® SYNERGY®) in the swine model," Skirball Center for Cardiovascular Research, Cardiovascular Research Foundation, Orangeburg, NY, USA, 2. CircuLite, Inc., Teaneck, NJ, USA; 3. Cedars Sinai Medical Center, Los Angeles, CA, USA, pp. 259-268.

* cited by examiner

INFLOW / OUTFLOW CANNULA ANCHORS

CROSS-REFERENCE TO RELATED APPLICATION

This application is a national phase application of PCT Application No. PCT/US2022/045771, internationally filed on Oct. 5, 2022, which claims the benefit of Provisional Application No. 63/253,402, filed Oct. 7, 2021, which are incorporated herein by reference in their entireties for all purposes.

FIELD

This disclosure relates generally to medical devices, and more specifically, to inflow or outflow cannulas that may include a tissue anchor.

BACKGROUND

Cannulas may be able to create flow conduits within a patient. For example, cannulas may be used to create flow conduits to or from an organ such as the heart. U.S. Pat. No. 10,849,653 to Tao et al., describes a cannula supporting a percutaneous pump that includes a proximal section with a first flexural modulus and one or more distal sections with a flexural modulus that is different than the first flexural modulus. The material and its arrangement along the length of the cannula can be selected so as to influence bending properties. This can, for example, allow efficient positioning of the cannula in a desired location without displacing the guidewire. Though Tao provides an example of one use, cannulas may be used in other contexts, such as for interconnecting or bypassing portions of the vasculature (e.g., between one or more vessels).

SUMMARY

According to one example ("Example 1"), a cannula includes a conduit having an exterior surface and an interior surface that includes a single piece of a first graft component arranged along the interior surface and being everted over a first end and a second end of the conduit to reduce disruption of fluid flow along the interior surface of the conduit to minimize thrombus formation and a support structure including an elongate element having a rectangular cross-section, the elongate element being coupled to the exterior surface of the conduit by a second graft component and extending along a length thereof to reduce thrombus formation along the exterior surface of the conduit. The cannula may include an optional, integrated collar arranged at one of the first end or the second end of the conduit configured to interface with another device. In some examples, the device is a pump device, such as a vascular pump or cardiac assistance device. The second end of the conduit may be configured to lessen an opportunity for deformation (e.g., expansion or collapse) of the conduit during operation of the pressure device to which the second end of the conduit is connected.

According to another example ("Example 2"), further to Example 1, the cannula further includes an anchoring structure arranged adjacent an end of the conduit configured to engage with tissue and anchor the conduit.

According to another example ("Example 3"), further to Example 2, the anchoring structure includes a first anchor portion having a stent portion extending along the exterior surface of the conduit to facilitate folding of the first anchor portion toward the exterior surface of the conduit in a delivery configuration, and a second anchor portion having a stent portion extending along the exterior surface of the conduit to facilitate folding of the second anchor portion toward the exterior surface of the conduit in the delivery configuration.

According to another example ("Example 4"), further to the cannula of Example 1, the optional, integrated collar includes a plurality of windows and a third graft component is arranged about the integrated collar at the plurality of windows to secure the integrated collar to the conduit.

According to another example ("Example 6"), further to the cannula of Example 1, the conduit is configured to interface with a pump, and the support structure is configured to resist collapse of the conduit during operation of the pump.

According to another example ("Example 6"), further to the cannula of Example 1, the interior surface of the conduit is configured to reduce thrombus formation having a substantially uninterrupted surface.

According to one example ("Example 7"), a cannula includes a conduit having an exterior surface and an interior surface, a proximal end and a distal end; an anchoring structure attached to the conduit adjacent an end of the conduit, the anchoring structure including: a first anchor portion having a plurality of first contact features and a first stent element extending along the exterior surface of the conduit toward the distal end of the conduit, and a second anchor portion having a plurality of second contact features and a second stent element extending along the exterior surface of the conduit toward the proximal end of the conduit, the first stent element being configured to facilitate folding of the first anchor portion toward the exterior surface of the conduit and adjacent the second stent element and the second stent element is configured to facilitate folding of the second anchor portion toward the exterior surface of the conduit and adjacent the first stent element in a delivery configuration According to another example ("Example 8"), further to the cannula of Example 7, the plurality of first contact features and the second plurality of contact features each include a first substantially linear section extending from the exterior surface of the conduit in a first direction, a second substantially linear section extending in a second direction, different than the first direction, to an apex, a third substantially linear section extending in a third direction opposite the second direction, and a fourth substantially linear section extending toward the conduit in a fourth direction opposite the first direction.

According to another example ("Example 9"), further to the cannula of Example 8, the first substantially linear section and the fourth substantially linear section are of approximately a common length.

According to another example ("Example 10"), further to the cannula of any one of Examples 8-9, the second substantially linear section and the third substantially linear section are of approximately a common length.

According to another example ("Example 11"), further to the cannula of Example 10, the length of first substantially linear section and the fourth substantially linear section is less the length of the second substantially linear section and the third substantially linear section.

According to another example ("Example 12"), further to the cannula of any one of Examples 7-11, a space between the first anchor portion and the second first anchor portion is between about 0 mm to about 2 mm.

According to another example ("Example 13"), further to the cannula of any one of Examples 7-12, the first anchor portion and the second anchor portion are configured to collapse toward the exterior surface of the conduit in the delivery configuration.

According to another example ("Example 14"), further to the cannula of any one of Examples 7-13, the first anchor portion includes a first stent element arranged along the exterior surface of the conduit, and the second first anchor portion includes a second stent element arranged along the exterior surface of the conduit.

According to another example ("Example 15"), further to the cannula of Example 14, the first stent element extends along the exterior surface of the conduit toward and past the second anchor portion and the second stent element extends along the exterior surface of the conduit toward and past the first anchor portion.

According to another example ("Example 16"), further to the cannula of any one of Examples 14-15, the first stent element is looped back toward the first anchor portion and the second stent element is looped back toward the second anchor portion.

According to another example ("Example 17"), further to the cannula of any one of Examples 7-16, each of the plurality of first contact features have a diamond shape and each of the plurality of second contact features have a diamond shape.

According to another example ("Example 18"), a cannula includes a conduit having an exterior surface and an interior surface; an anchoring structure arranged adjacent an end of the conduit configured to engage with tissue and anchor the conduit, the anchoring structure including: a first anchor portion having a plurality of first contact features extending longitudinally outward relative to the exterior surface of the conduit and a stent portion extending along the exterior surface of the conduit to facilitate folding of the first anchor portion toward the exterior surface of the conduit and in a first direction in a delivery configuration, and a second anchor portion having a plurality of second contact features extending longitudinally outward relative to the exterior surface of the conduit and a stent portion extending along the exterior surface of the conduit to facilitate folding of the second anchor portion toward the exterior surface of the conduit and in a second direction opposite the first direction in the delivery configuration.

According to another example ("Example 19"), further to the cannula of Example 18, the first stent element extends along the exterior surface of the conduit toward and past the second anchor portion and the second stent element extends along the exterior surface of the conduit toward and past the first anchor portion.

According to another example ("Example 20"), further to the cannula of any one of Examples 18-19, the first stent element is looped back toward the first anchor portion and the second stent element is looped back toward the second anchor portion.

According to another example ("Example 21"), further to the cannula of any one of Examples 18-20, the first stent element is configured to facilitate folding of the first anchor portion toward the exterior surface of the conduit and adjacent the second stent element and the second stent element is configured to facilitate folding of the second anchor portion toward the exterior surface of the conduit and adjacent the first stent element in the delivery configuration.

According to another example ("Example 22"), further to the cannula of any one of Examples 18-21, the plurality of first contact features and the second plurality of contact features each include a first substantially linear section extending from the exterior surface of the conduit in a first direction, a second substantially linear section extending in a second direction, different than the first direction, to an apex, a third substantially linear section extending in a third direction opposite the second direction, and a fourth substantially linear section extending toward the conduit in a fourth direction opposite the first direction.

According to another example ("Example 23"), further to the cannula of any one of Examples 18-22, further including a connector that is integrated to the conduit configured to facilitate attachment to a pump and reduction of thrombus formation.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1:
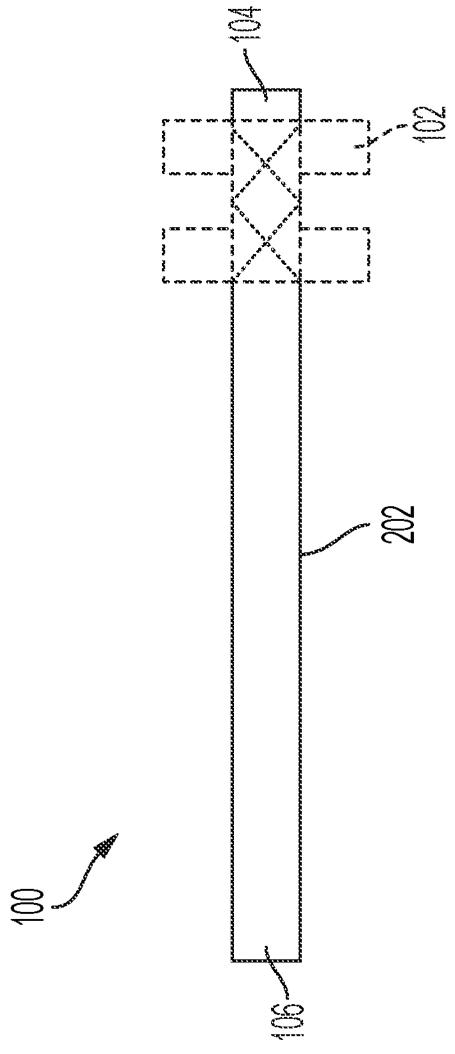
FIG. 1 is an illustration of an example cannula and anchoring structure, in accordance with various aspects of the present disclosure.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value or that of one skilled in the art's understanding.

DESCRIPTION OF VARIOUS EMBODIMENTS

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed to apparatuses, systems, and methods that include a cannula. The cannula may be arranged within a patient and create a fluid passageway. The cannula may extend from an organ (e.g., vasculature, heart, gallbladder, liver, or lungs) and connect to a device, another organ or bodily structure, or exit the patient. In certain instances, the cannula may be a graft or stent graft that is arranged within the vasculature. The apparatuses, systems, and methods may be used in improving or assisting vascular and/or the cardiac function of the body. The cannula, as discussed in further detail below, may include an anchoring structure. The anchoring structure may be arranged to anchor with a tissue between two compartments (e.g., two vessels, heart chambers, or other bodily structures) within a patient. The anchoring structure may be arranged between vessels or between different portions of the same vessel, or on either side of a septum within a patient's heart, for example. The disclosed anchoring structure or inlet portion of a cannula may be used with a pump device, such as a vascular pump or a circulatory assist device for managing (e.g., increasing) blood flow in a patient.

Circulatory assist devices are just one known type of device for increasing blood circulation. Unlike replacement with a total artificial heart (TAH)—when a patient's heart is removed and replaced by an artificial heart—the patient's heart remains and is assisted by a circulatory assist device. The device may be configured to support both cardiac ventricles, with one pump for each cardiac chamber-thus named biventricular assist devices (BVAD). Left ventricular assist devices (LVADs) and right ventricular assist devices (RVAD) support the left or right sides of the heart. Embodiments described herein can be used with circulatory assist devices, or any of a variety of pump devices.

FIG. 1 is a schematic illustration of an example cannula 100 including an anchoring structure 102, in accordance with various aspects of the present disclosure. The anchoring structure 102 may be used for an inflow or outflow cannula. Or, in different terms, the cannula may be configured as an inflow cannula that conveys fluid into a desired location (e.g., a pump or circulatory assist device) or an outflow cannula that conveys fluid from a desired location (e.g., a pump or circulatory assist device). As shown, the cannula 100 has a first end 104 and a second end 106 opposite the first end 104. In certain instances, the anchoring structure 102 may be arranged closer to the first end 104 of the cannula than 100 the second end 106 of the cannula 100. For example, the anchoring structure 102 may be located at or near the first end 104 of the cannula 100.

The anchoring structure 102 may include a single flange extending circumferentially outwardly from the cannula 100 or a plurality of flanges (e.g., a dual flange structure as illustrated generally in FIG. 1) extending circumferentially outwardly from the cannula 100 and/or a support structure arranged along a portion of the cannula 100 (e.g., on the outside of the cannula 100). The anchoring structure 102 may be configured to transition from a collapsed, delivery configuration to an expanded, deployed configuration. Portions of the anchoring structure 102 may be self-expanding, balloon expandable, or one or more portions of the anchoring structure 102 being self-expanding and one or more balloon expandable. The anchoring structure 102 may facilitate against kinking or collapse of the end of the cannula 100 by reinforcing the cannula 100.

The cannula 100 may include a conduit 202 that is formed of biocompatible material, such as a graft material, and the anchoring structure 102 may be formed of biocompatible material, such as that associated with stent elements and/or graft materials.

In certain instances, the conduit 202 may be relatively inextensible or may be configured to stretch to adjust in size, or may be configured to be stretched in response to forces acting on the conduit 202 and recover all or some portion of its length upon removal or reduction of such forces acting on the conduit 202. Further discussion of the graft portion 108 may be found in U.S. Pat. No. 4,877,661 ("House, et al."), although a variety of suitable materials are contemplated.

Any number of cannulas may be implemented, and the disclosure is not to be limiting on the scope of the cannula. In one example, the cannula 100 is formed of a graft structure that may include reinforcing elements such as rings or a helical structure (e.g., helically wound wire or a tube with a helical cut extending around and longitudinally along the length of the cannula 100*m* bare stent, or partially covered stent, or covered stent). In some embodiments, the cannula 100 may include a coating or material (e.g., a graft material such as, but not limited to ePTFE or another fluoropolymer based graft material) for forming a fluid impermeable barrier for the cannula 100.

Figure 2A:
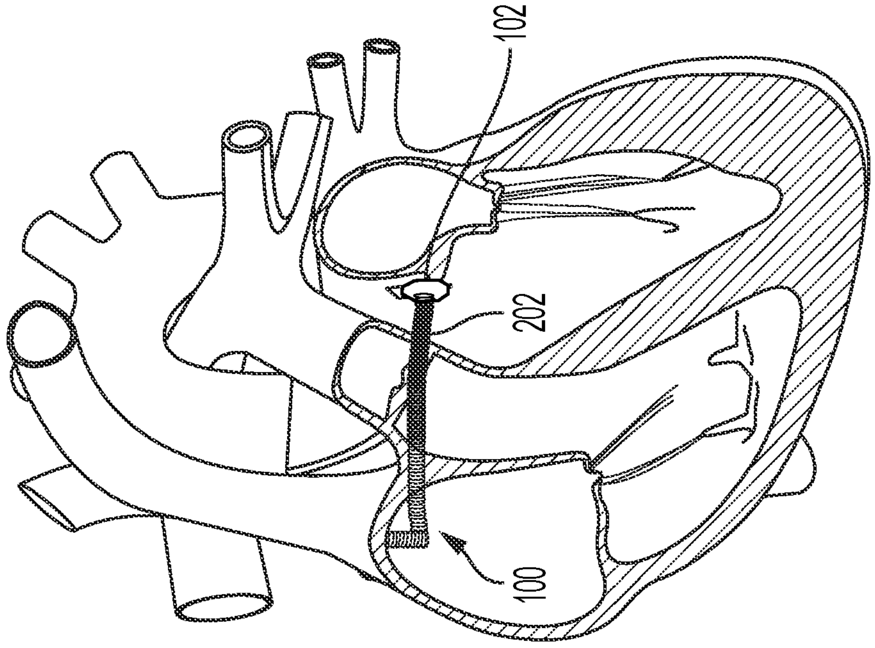
FIGS. 2A-2B are illustrations of an example cannulas arranged within a patient's heart, in accordance with various aspects of the present disclosure.

FIG. 2A is an illustration of an example of the cannula 100 shown arranged within a patient's heart, according to some embodiments. In the example shown, the cannula 100 may be used for an inflow or outflow cannula. As shown, the anchoring structure 102 is arranged at or adjacent to an end of the conduit 202 of the cannula 100. The conduit 202 may be configured to provide a fluid passageway from or to a target location or between two target locations.

In certain instances, and as is shown, the anchoring structure 102 is engaged with a septum of a patient's heart. In certain instances, the conduit 202 may be anchored within a pulmonary vein of a patient. In other instances, the anchoring structure 102 may be arranged to anchor with another organ, tissue structure, septum, tissue wall, or within the vasculature of the patient. The anchoring structure 102 can be utilized to connect two or more structures in a human body, such as organ, heart, and vasculature, aorta, in addition to its configuration to anchor the cannula.

Figure 2B:
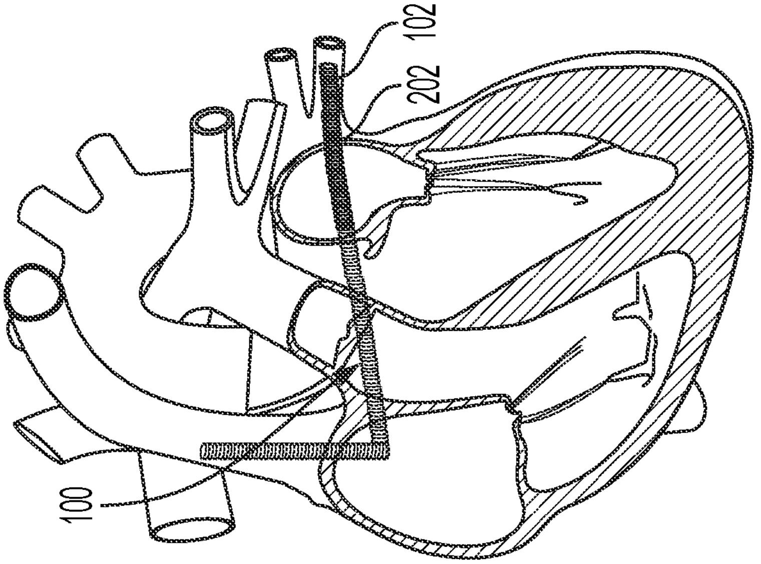

FIG. 2B shows another example positioning of the cannula 100 at a target location within the patient's heart. The cannula 100 may include a stent (anchor 102) element, as described above with reference to FIG. 1, that may be configured to anchor the cannula 100 within the pulmonary vein. The stent may be a covered stent, bare stent, or partially covered stent. The cannula 100, when connected to a pump, may pull blood from either the pulmonary vein or the left atrium through the cannula 100 toward the pump.

Figure 3B:
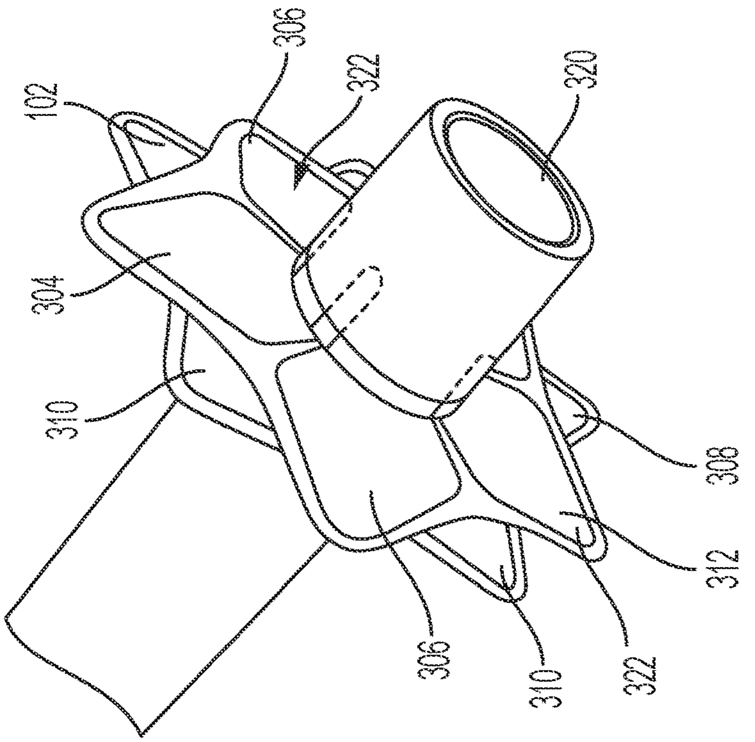
FIGS. 3A-3B is an illustration of an example cannula and anchoring structure, in accordance with various aspects of the present disclosure.
Figure 3A:
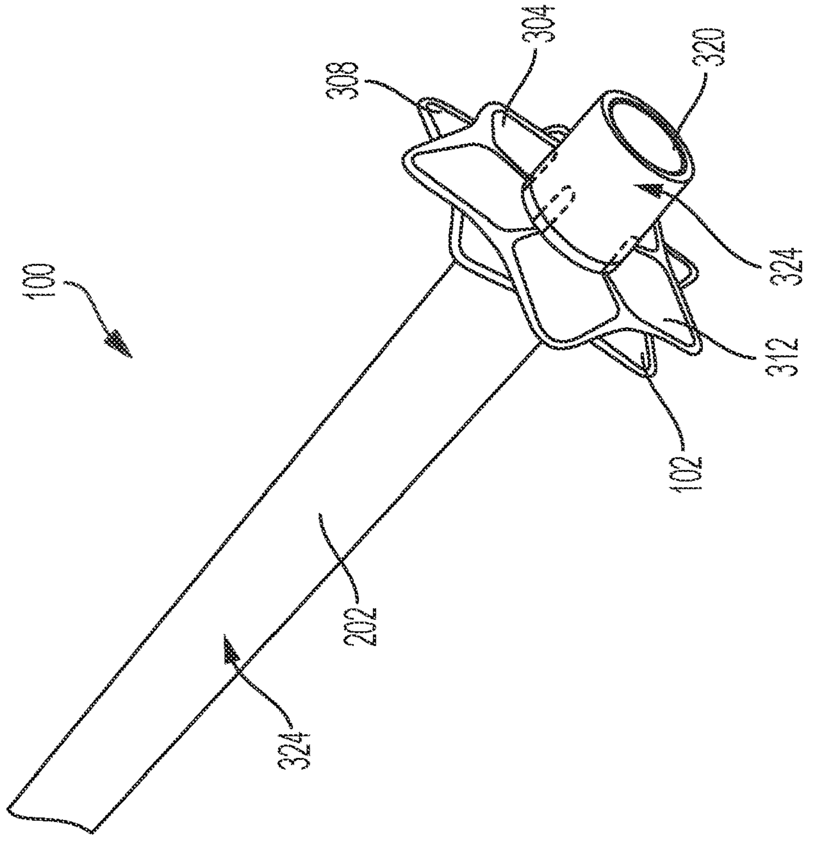

FIG. 3A is an illustration of an example of the cannula 100 and included anchoring structure 102, and FIG. 3B is an enlarged view of a portion of the cannula 100 at the anchoring structure 102, in accordance with various aspects of the present disclosure. As shown in FIG. 3A, the cannula 100 includes a conduit 202 and has an exterior surface and an interior surface with the anchoring structure 102 being arranged adjacent an end of the conduit 202. As shown in FIG. 3B, the anchoring structure 102 may include a first anchor portion 304 having a plurality of first contact feature 306 and a second anchor portion 308 having a plurality of second contact feature 310. As shown, the first anchor portion 304 and the second anchor portion 308 are positioned opposite one another, and are generally configured as opposing flanges configured to press against tissue to serve an anchoring function when deployed in the body.

In certain instances, each of the plurality of first contact feature 306 and each of the plurality of second contact feature 310 may have a diamond shape, though a variety of shapes are contemplated. In addition, and as is shown, the plurality of first contact features 306 and the plurality of second contact features 310 may project radially outward from a point of origin that is offset relative to a longitudinal axis of the conduit.

As shown in FIGS. 3A and 3B, and as previously referenced in association with various examples, the conduit 202 may include a graft component 320. In addition, the anchoring structure 102 may include a graft component 312 that covers and/or extends between one or more open spaces 322 (FIG. 3B) defined by each of the plurality of first contact features 306 and the plurality of second contact features 310. In certain instances, the first anchor portion 304 and the second anchor portion 308 may be configured to fold or collapse toward the exterior surface 324 of the conduit 202 in a delivery configuration. The contact features 306, 310 may be formed of a stent structure and the graft component 320 may cover the stent structure. The first anchor portion 304 may fold toward the exterior surface 324 of the conduit 202 and in a first direction in a delivery configuration, and the second anchor portion 308 toward the exterior surface 324 of the conduit 202 and in a second direction opposite the first direction in the delivery configuration.

Figure 4:
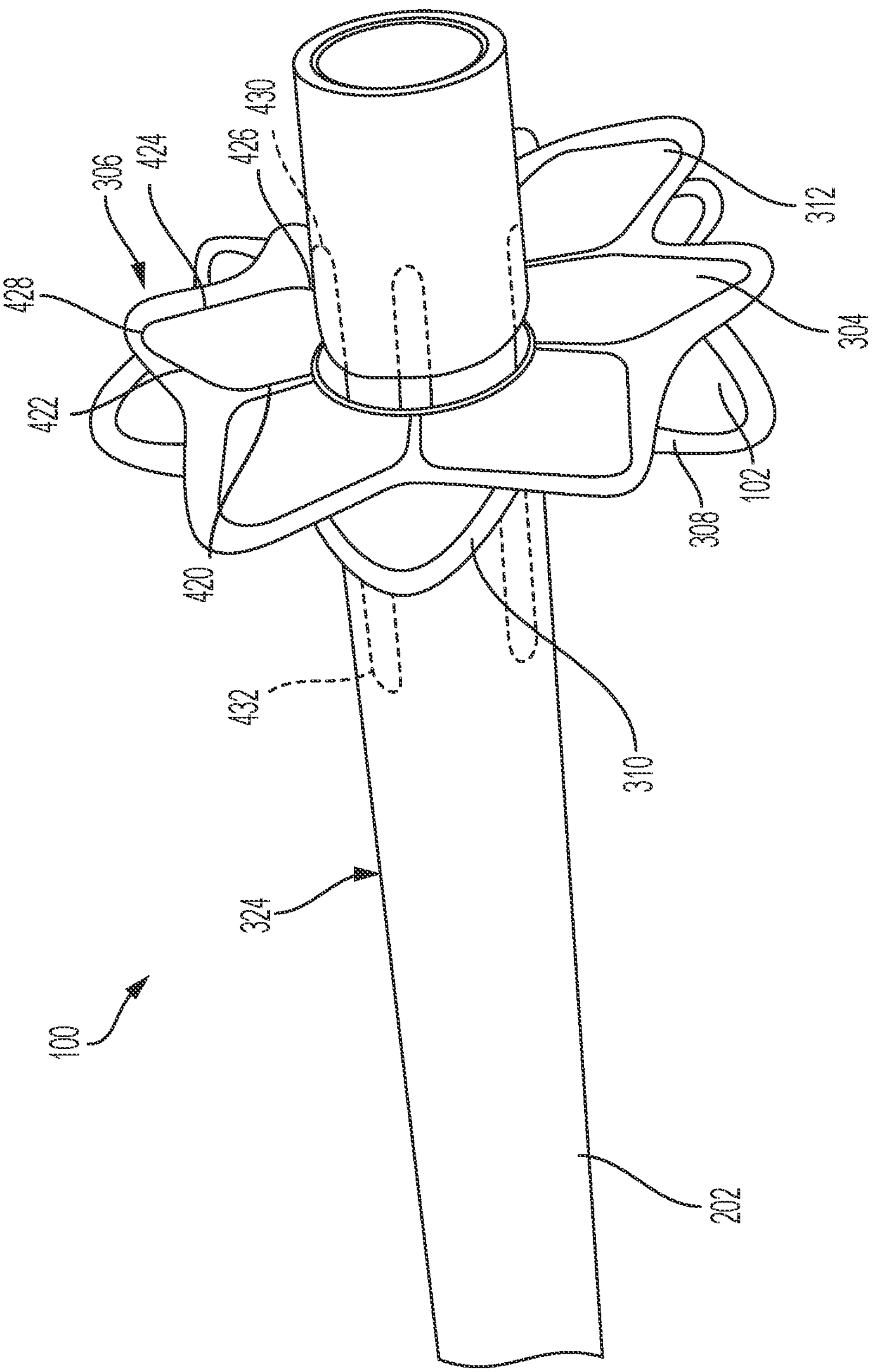
FIG. 4 is a close-up illustration of an example cannula and anchoring structure, in accordance with various aspects of the present disclosure.

FIG. 4 is a close up illustration of an example of the cannula 100 and anchoring structure 102, in accordance with various aspects of the present disclosure. As shown, a portion of the conduit 202 is not depicted and the anchoring structure 102 is arranged at or adjacent to an end of the conduit 202, which may be configured to provide a fluid passageway to or from a target location or between to target locations.

In certain instances, and as is shown, the anchoring structure 102 is configured to anchor to a septum within the patient's heart. In certain instances, the conduit 202 may be anchored within or extends through the pulmonary vein of a patient. In other instances, the anchoring structure 102 may be arranged with another organ, tissue structure, septum, tissue wall, or within the vasculature of the patient.

As previously referenced, the anchoring structure 102 may include a first anchor portion 304 having a plurality of first contact features 306 and a second anchor portion 308 having a plurality of second contact features 310. In certain instances, each of the plurality of first contact features 306 and the plurality of second contact features 310 may include a common shape, or in different terms, each may have substantially the same shape as the others. In certain instances, the shape of the plurality of first contact features 306 and the plurality of second contact features 310 differ in shape, or are of a different shape than one another.

As shown, in the deployed, or expanded state, each of the plurality of first contact features 306 and each of the plurality of second contact features 308 projects radially outward relatively to a central longitudinal axis of the cannula 100. In certain instances, the plurality of first contact features 306 and the second plurality of contact features 308 each include a first substantially linear section 420 extending from the exterior surface of the conduit 202 in a first direction, a second substantially linear section 422 extending in a second direction, different than the first direction, to an apex 428 of each of the plurality of first contact features 306 and the second plurality of contact features 308. In addition, the plurality of first contact features 306 and the second plurality of contact features 308 may include a third substantially linear section 424 extending in a third direction opposite the second direction, and a fourth substantially linear section 426 extending toward the conduit 202 in a fourth direction opposite the first direction. The plurality of first contact features 306 and the second plurality of contact features 308 may each include a diamond or an approximate diamond shape. In certain instances, the diamond shape of the plurality of first contact features 306 and the second plurality of contact features 308 facilitates crushing or containment of the plurality of first contact features 306 and the second plurality of contact features 308 against the cannula 100 in a delivery configuration. In addition, and as noted above, the plurality of first contact features 306 and the second plurality of contact features 308 may be covered by the graft component 320. The diamond shape of the plurality of first contact features 306 and the second plurality of contact features 308 may provide stability and while avoiding stretching of the graft component 320.

In certain instances, the first substantially linear section 420 and the fourth substantially linear section 426 are of approximately a common length. In addition, the second substantially linear section 422 and the third substantially linear section 424 may be of approximately a common length. In certain instances, the length of first substantially linear section 420 and the fourth substantially linear section 426 is less the length of the second substantially linear section 422 and the third substantially linear section 424.

In certain instances, the first anchor portion 304 and the second anchor portion 308 are configured to collapse from an outwardly-extending configuration toward the exterior surface of the conduit 202 (e.g., to lay against the exterior surface 324 of the conduit 202) when the anchoring structure 102 transitioned from a deployed configuration to a delivery configuration. As described in further detail below with reference to FIG. 5, the first anchor portion 304 may include a first stent element 432 arranged along the exterior surface of the conduit 202, and the second anchor portion 308 includes a second stent element 430 arranged along the exterior surface of the conduit 202 (e.g., being at least partially covered by an outer layer of material, such as a film or tape).

In certain instances, the first stent element 432 extends from the first anchor portion 304 along the exterior surface of the conduit 202 (e.g., being at least partially covered by an outer layer of material, such as a film or tape) toward and past the second anchor portion 308 (toward the distal end of the conduit 202) and the second stent element 430 extends of the second anchor portion 308 along the exterior surface of the conduit 202 toward and past the first anchor portion 304 (toward a proximal end of the conduit 202). As shown, the first and second stent elements 432, 430 may each define an undulating pattern extending through a path defining a plurality of turns. In different terms, the first stent element 432 is loops back and forth toward and away from the first anchor portion 304 and the second stent element 430 loops back and forth toward and away from the second anchor portion 308 as shown in FIG. 4. The loops, or turns of each of the first stent element 432 and the second stent element 430 define a plurality of stent structures that are arranged about a circumference of the conduit 202 as shown. The plurality of stent structures of each of the first stent element 432 and the second stent element 430 may be equal to the number of contact features 306, 310 of the first anchor portion 304 and the second anchor portion 308, or may be different as desired.

The first stent element 432 and the second stent element 430 may be coupled to the conduit 202 by a graft layer as shown in FIG. 4. s first stent element 432 and the second stent element 430 may be held against the conduit 202 and, as the first and second anchoring portions 304, 308 are connected to the first and second stent elements 432, 430, respectively, may assist in securing the first and second anchoring portions 304, 308 relative to the conduit 202. In certain instances, the first stent element 432 and the second stent element 430 may structurally enhance the conduit 202 where the anchoring structure 102 is coupled to the conduit 202 by the first and second stent elements 432, 430.

As shown, a distal end portion 320 of the conduit 202 may extend distal of, or beyond the anchoring structure 102. The distal end portion 320 may define a length that is configured or otherwise selected to avoid tissue ingrowth along the conduit 202 that could otherwise obstruct the inlet of the conduit 202 (which corresponds to the distal end portion 320 as shown). In certain instances, the distal end portion 320 of the conduit 202 may have a length that is selected to avoid or is biased to avoid suctioning or obstructing the anatomy of the heart (e.g., valve leaflets). The distal end portion 320 is configured to extend into the heart without contacting other areas of the heart that could affect the heart performance. In certain instances, the distal end portion 320 of the conduit 202 may end between about 5 mm to about 10 mm beyond the second anchoring portion 308. In addition, the distance between the first and second anchoring portions 304, 308 may be between about 0 mm to 2 mm, in certain instances. in addition, the distal end portion 320 of the conduit 202 may include a graft component 320 that includes a closed structure that avoids tissue ingrowth. The graft component 320 arranged with the first and second anchoring portions 304, 308 may be an open structure configured to facilitate tissue ingrowth. The remaining portions of the component 320 along an exterior surface of the conduit 202 (e.g., proximal to the first anchoring portion 304) may also include a closed structure that avoids tissue ingrowth.

Figure 5:
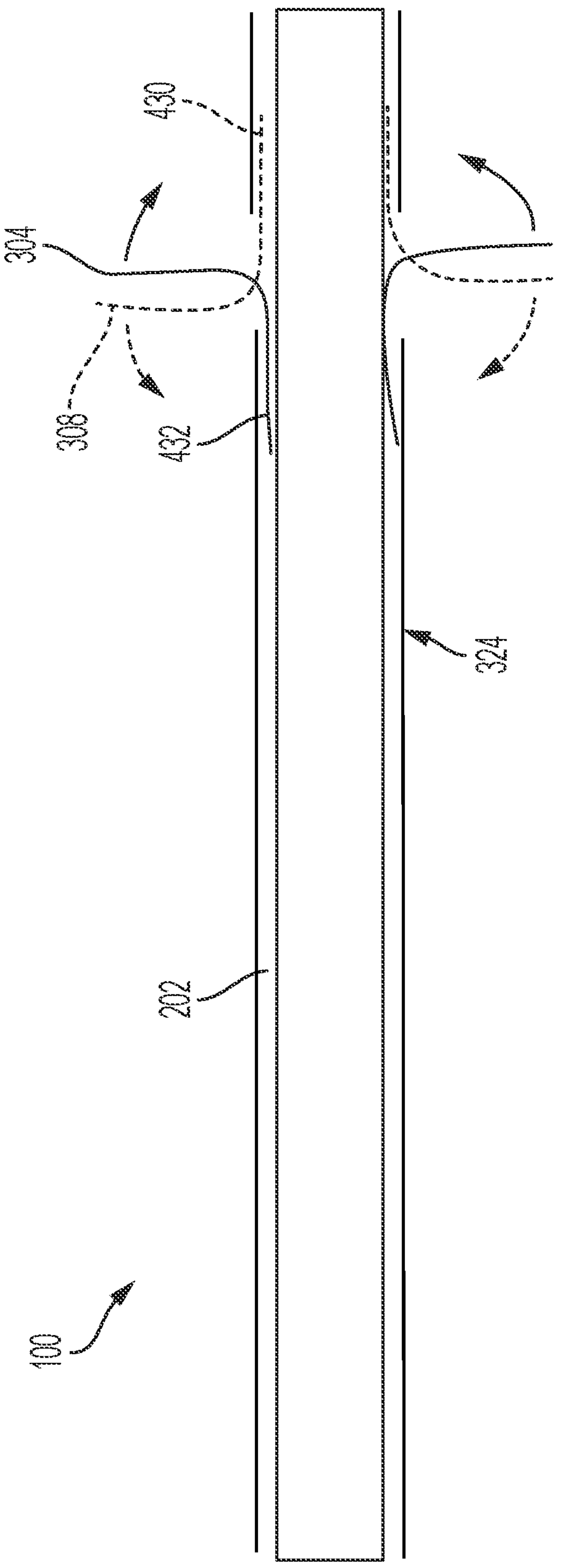
FIG. 5 is an illustration of an example anchoring structure and constraining directions, in accordance with various aspects of the present disclosure.

FIG. 5 is a schematic illustration of an example of the anchoring structure 102 and manner in which the anchoring structure 102 is transitioned between a collapsed, delivery configuration to an expanded, deployed configuration. As discussed in detail above, the anchoring structure 102 may be part of cannula 100 which that includes conduit 202 having an exterior surface and an interior surface. The anchoring structure 102 is arranged adjacent an end portion of the conduit 202 and is configured to engage with tissue and anchor the conduit 202.

The anchoring structure 102, as discussed in detail above, includes a first anchor portion 304 having a plurality of first contact features extending longitudinally outward relative to the exterior surface of the conduit 202 (as shown in FIG. 4) and a first stent portion 432 extending along the exterior surface of the conduit 202 to facilitate folding of the first anchor portion 304 toward the exterior surface of the conduit 202 in a delivery configuration. The anchoring structure 102 also includes a second anchor portion 308 having a plurality of second contact features extending longitudinally outward relative to the exterior surface of the conduit 202 (as shown in FIG. 4) and a second stent portion 430 extending along the exterior surface of the conduit 202 to facilitate folding of the second anchor portion 308 toward the exterior surface of the conduit 202 in the delivery configuration.

In certain instances, the first stent element 432 extends along the exterior surface of the conduit 202 toward and past the second anchor portion 308 and the second stent element 430 extends along the exterior surface of the conduit 202 toward and past the first anchor portion 304. The first stent element 432 is configured to facilitate folding of the first anchor portion 304 toward the exterior surface of the conduit 202 and adjacent the second stent element 430 and the second stent element 430 is configured to facilitate folding of the second anchor portion 308 toward the exterior surface of the conduit 202 and adjacent the first stent element 432 in the delivery configuration.

Figure 6A:
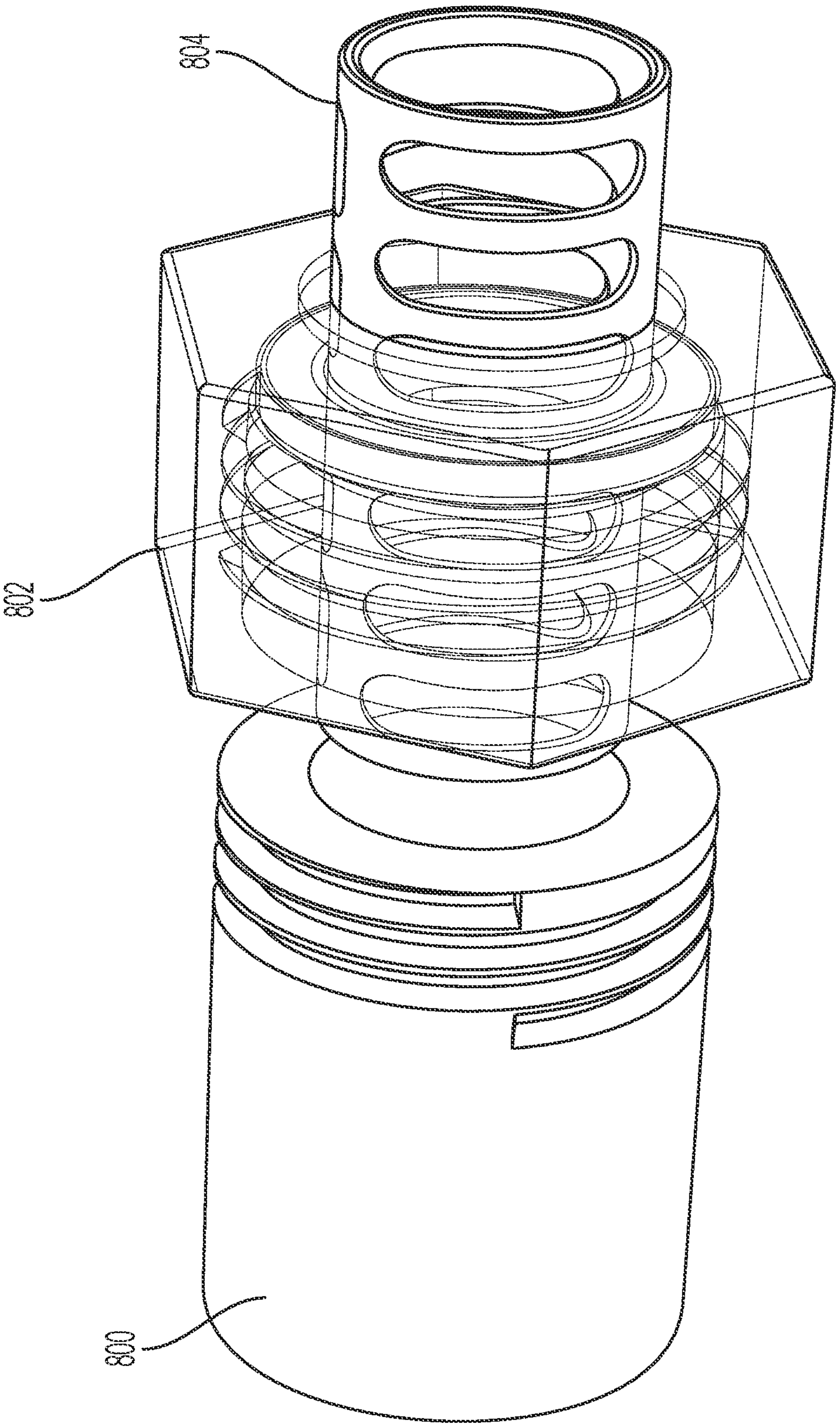
FIG. 6A is an illustration of an example pump inlet and integrated collar of a cannula, in accordance with various aspects of the present disclosure.

FIG. 6A is an illustration of an example pump inlet 800 and integrated collar 804, in accordance with various aspects of the present disclosure. 8B shows the example pump inlet 800 and a cannula 100. The integrated collar 804 may be attached or coupled to the cannula 100 (shown in FIG. 6B) and may be configured to create an interface between the cannula and the pump inlet 800 that lessens the opportunity for thrombus formation.

Figure 6B:
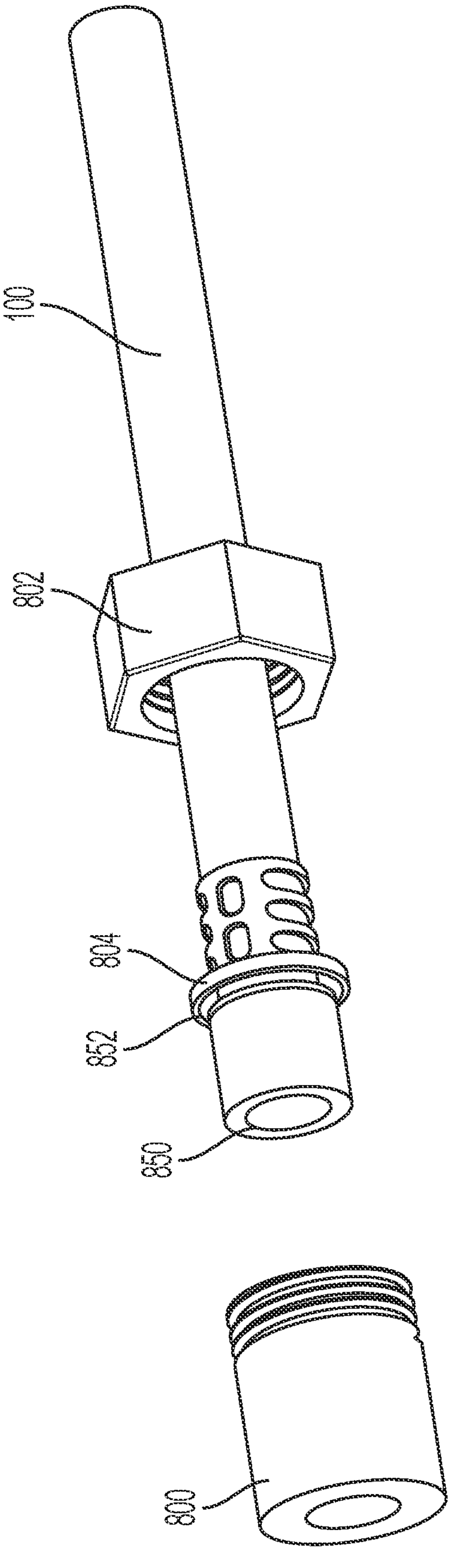
FIG. 6B is an illustration of the pump inlet and integrated collar, shown in FIG. 8A, with a cannula, in accordance with various aspects of the present disclosure.

In certain instances, the integrated collar 804 may be configured to transition the cannula to the pump inlet 800 approximately without change in diameter as shown in FIG. 6B between the pump inlet 800 and the cannula to lessen the risk of thrombus formation. In certain instances, the integrated collar 804 may facilitate attachment between the pump inlet 800 and the cannula by attaching the cannula to the pump inlet 800 by a quick connect threaded component 802. In certain instances, the integrated collar 804 also facilitate sealing off any blood from leaking out of the cannula-pump interface connection.

In certain instances, the integrated collar 804 may be attached to the cannula by a graft member wrapped about the integrated collar 804 and the cannula (e.g., FEP film). The integrated collar 804 may be a connector that is integrated to the conduit configured to facilitate attachment to a pump and reduction of thrombus formation.

As shown in FIG. 6B, a proximal end 850 of the conduit 202 that includes a greater diameter than other portions of the conduit 202. This is shown in further detail in FIG. 8. The proximal end 850 may be slid into the pump inlet 800 and include matching diameters to facilitate blood flow without disturbance therethrough. The proximal end 850 may reduce a step or difference in diameter between the cannula 100 and the pump inlet 800. A o-ring 852 may be arranged with the integrated collar 804 to lessen leakage between the cannula 100 and the pump inlet 800. The hex nut 802 may slide along the cannula 100 and couple the cannula 100 to the pump inlet 800.

Figure 7A:
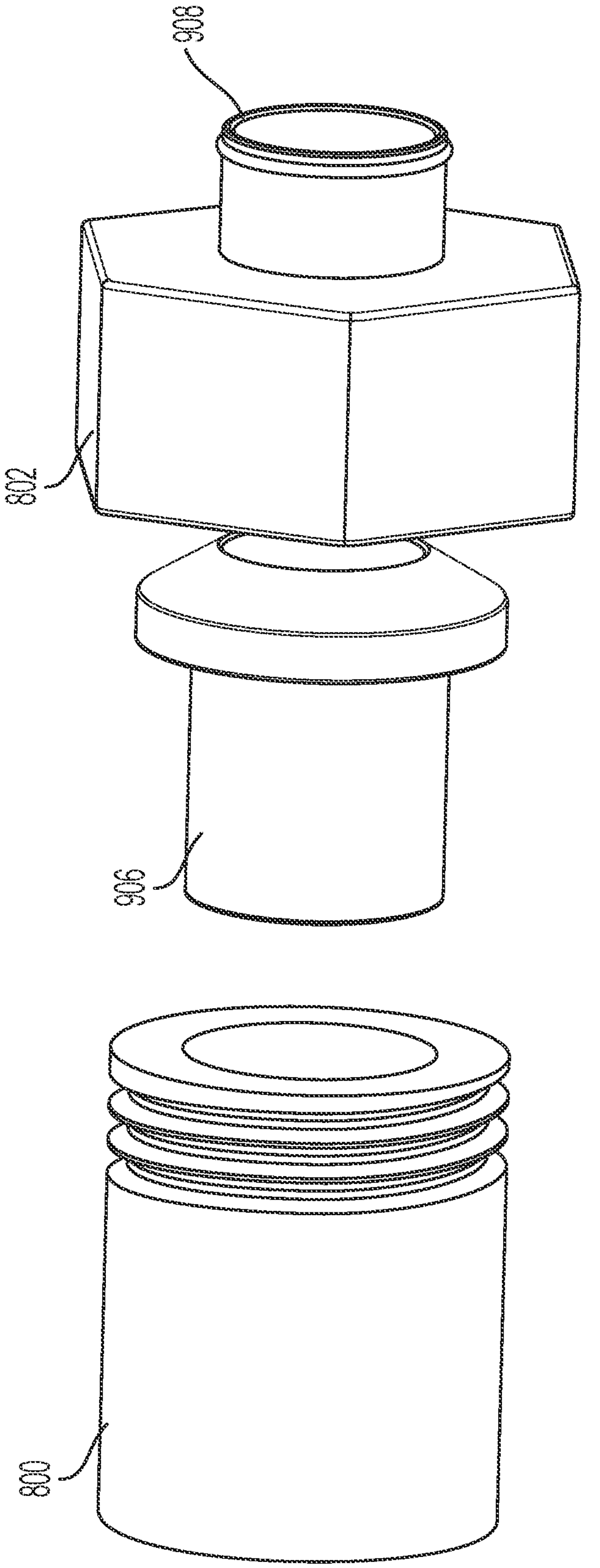
FIG. 7A is another illustration of an example pump inlet, internal component, and pump inlet extension for a cannula, in accordance with various aspects of the present disclosure.
Figure 7B:
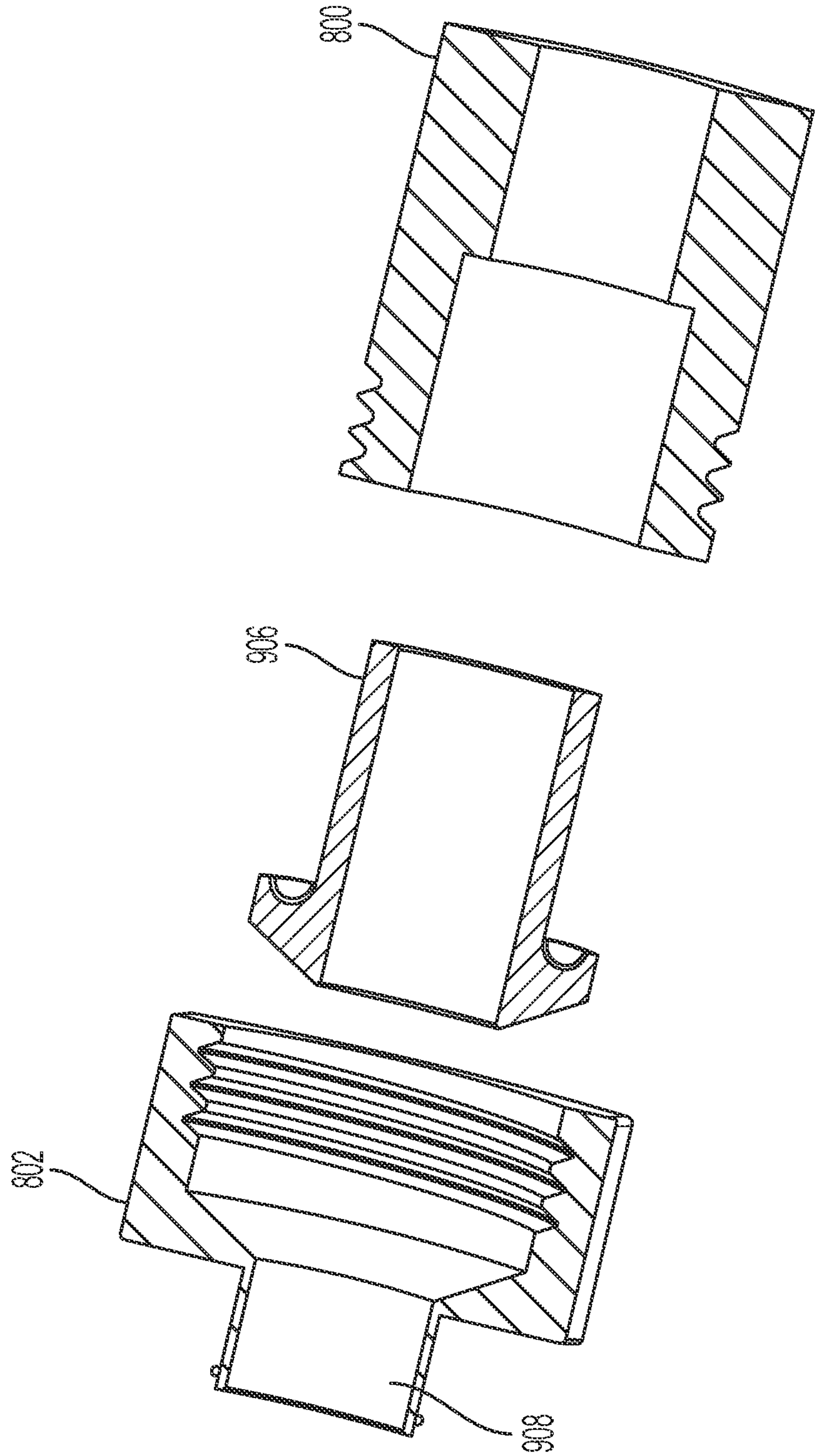
FIG. 7B is a cross-sectional illustration of the example pump inlet, internal component, and pump inlet extension, shown in FIG. 7A, in accordance with various aspects of the present disclosure.

FIG. 7A is another illustration of an example pump inlet 800 and internal component 906, and pump inlet extension 908, in accordance with various aspects of the present disclosure. The internal component 906 may be configured to transition the cannula to the pump inlet 800 approximately without change in diameter between the pump inlet 800 and the cannula to lessen the risk of thrombus formation. In certain instances, the threaded component 802 may facilitate attachment between the pump inlet 800 and the cannula by attaching the cannula to the pump inlet 800 by a quick connect threaded component 802. In certain instances, the internal component 906 also facilitate sealing off any blood from leaking out of the cannula-pump interface connection.

The pump inlet extension 908 may be coupled to a cannula to connect the pump inlet 800 and the cannula together. The pump inlet extension 908 may be arranged within an end portion of the cannula. A clamp (e.g., as shown in FIG. 6) may be arranged about the cannula, slid over the pump inlet extension 908, to secure the cannula to the pump inlet extension 908.

Figure 8:
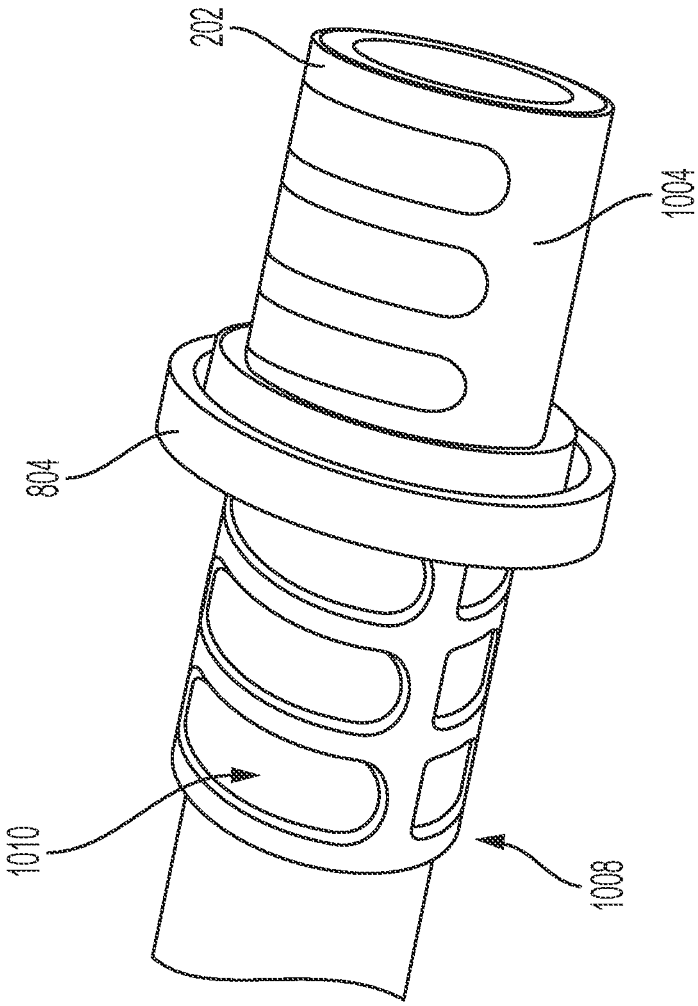
FIG. 8 is an illustration of an example cannula locking collar for coupling a cannula to a pump, in accordance with various aspects of the present disclosure.

FIG. 8 is an illustration of an example locking collar 804 (shown in FIG. 6) for a cannula 100 and pump, in accordance with various aspects of the present disclosure. The integrated locking collar 804 is shown coupled to a conduit 202. In certain instances, and as noted above, the conduit 202 may be formed of one or more graft components. The graft component 1004 of the conduit 202 may be arranged through the integrated collar 804 and everted over the end of the integrated collar 804 as shown in comparing a proximal end 850 (FIG. 6B) of the integrated collar 804 to a proximal end 1008 of the integrated collar 804.

In certain instances, the proximal end 850 and/or the proximal end 1008 of the integrated collar 804 may include windows or openings 1010. The windows or openings 1010 may facilitate attachment between the integrated collar 804 and the conduit 202. A graft component may be arranged about the proximal end 1008 of the integrated collar 804 with the windows or openings 1010 (at least some of which are covered in FIG. 8 by the graft component 1004 everted over the integrated collar 804) allowing coupling or adhesive attachment (e.g., using Fluorinated ethylene propylene (FEP)) between the graft component and the conduit 202.

In certain instances, the integrated collar 804 may facilitate maintaining the lumen of the conduit 202 open during pump cycles. The connecting between the conduit 202 and the pump (not shown) may have a large amount of force during cycling of the pump, and the integrated collar 804 (which may have a greater stiffness or radial strength that the conduit 202) may resist collapse of the conduit 202 at that point. The integrated collar 804 may add stiffness and kink resistance at the pump-to-conduit interface. The integrated collar 804 may also facilitate ease of connection of the pump.

Figure 9:
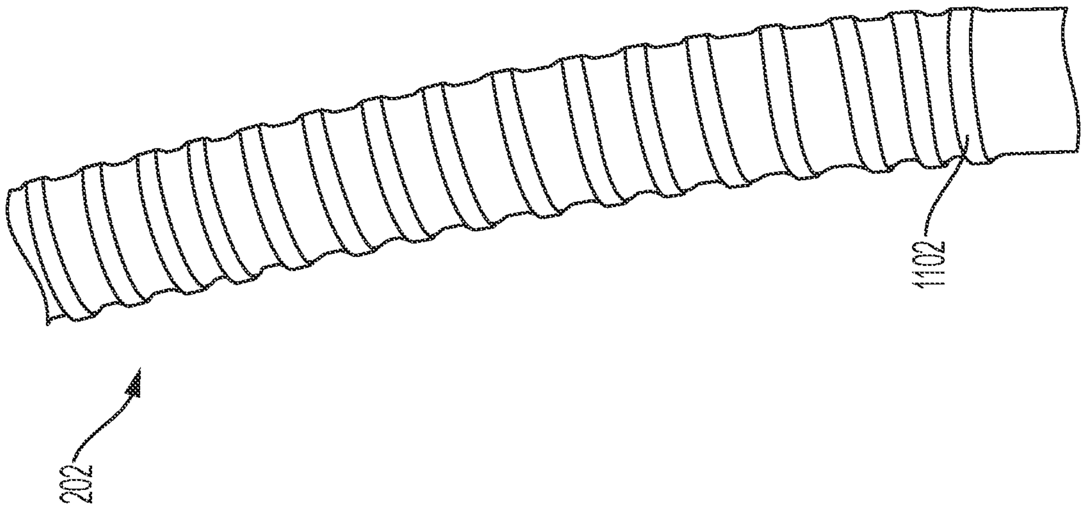
FIG. 9 is an illustration of an example cannula and stent, in accordance with various aspects of the present disclosure.

FIG. 9 is an illustration of an example cannula 100 and support structure 1102, in accordance with various aspects of the present disclosure. When utilized with circulatory assist devices embodiments herein are configured to minimize thrombus formation by a) providing interior surface that comprises a single component material to avoid transitions between materials that may have areas where thrombus formation may occur due to gaps between materials or structures that would disturb blood flow and cause turbulence, for example; b) when multiple materials are used on the interior surface the materials are selected to provide a substantially smooth surface for the blood to flow across and disruptions in any junctures in materials/components are minimized; and c) reducing the cannula's ability to resist collapsing and/or kinking when implanted in the body such as by use of reinforcing flat wire, flat stents, or as in other embodiments disclosed herein. The conduit 202 of the cannula 100 may include an interior surface that is configured to reduce thrombus formation. The interior surface of the conduit 202 may be substantially smooth or wrinkle free to avoid thrombus formation. The interior surface of the conduit 202 may be a single piece or run of graft material in certain instances to minimize thrombus formation. As noted above, the conduit 202 may include a collar or other aspects to connect to the pump in order to maintain laminar flow and avoid thrombus and turbulence within the conduit 202. In certain instances, the interior surface of the conduit 202 may be treated with heparin to avoid thrombosis.

The support structure 1102 may include an elongate member having a substantially rectangular cross-section, or in different terms, a flat wire, that extends about a circumference of the exterior surface of the conduit 202. The support structure 1102 may provide radial strength to the conduit 202 (e.g., being biased toward an open configuration).

The flat stent 1102, in certain instances, is configured to resist collapse of the conduit 202 during operation of the pump. For example, the support structure 1102 may be configured to avoid foreshortening and collapse of the conduit 202 during pump operation by being biased toward a radially expanded state to provide radial and longitudinal reinforcement to the conduit 202. The support structure 1102 may be configured to provide such reinforcement to the conduit 202 to resist collapse while also allowing for flattening and compression of the conduit 202 (e.g., using a forceps, pincers, or other tool) to allow for blocking/closing of the conduit 202 at a desired time (e.g., during connection to the pump, for example). The support structure 1102 may be self-expanding to allow for crush and re-expansion. In this regard, the support structure 1102 may also avoid kinking of the conduit 202 during implant.

Figure 10:
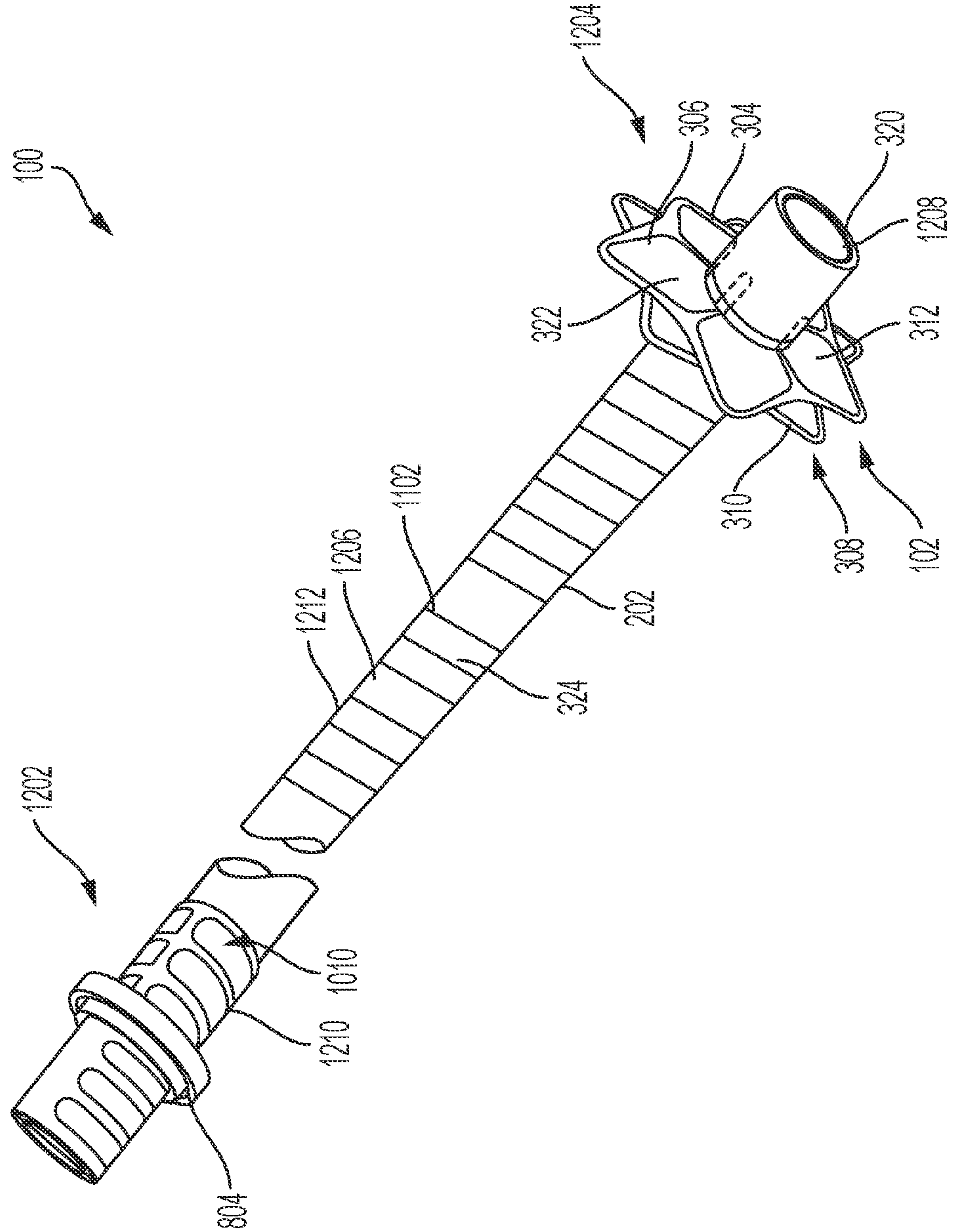
FIG. 10 is an illustration of an example cannula, in accordance with various aspects of the present disclosure.

FIG. 10 is an illustration of an example cannula 100, in accordance with various aspects of the present disclosure. As shown, the cannula 100 includes a first end 1202 that includes a locking collar 804 for coupling the cannula 100 to a pump (not shown) and a second end 1204 that includes an anchoring structure 102. The cannula 100 may extend between the first end 1202 and the second end 1204 and include an exterior surface 1206 and an interior surface 1208.

As discussed in detail above, the anchoring structure 102 is arranged adjacent an end (the second end 1204) of a conduit 202 that forms a fluid passageway for the conduit 100 between the first end 1202 and the second end 1204 of the cannula 100. The anchoring structure 102 may include a first anchor portion 304 having a plurality of first contact feature 306 and a second anchor portion 308 having a plurality of second contact feature 310. As shown, the first anchor portion 304 and the second anchor portion 308 are positioned opposite one another, and are generally configured as opposing flanges configured to press against tissue to serve an anchoring function.

In certain instances, each of the plurality of first contact feature 306 and each of the plurality of second contact feature 310 may have a diamond shape, though a variety of shapes are contemplated.

As previously referenced in association with various examples, the conduit 202 may include one or more graft components. A first graft component 320 may be arranged along the interior surface 1208 of the cannula 100. The first graft component 320 may be everted over each of the first end 1202 and the second end 1204 of the cannula 100 to create a device that is smooth and without steps, seams, or additional tip pieces. The interior surface 1208, as a result, may be configured to reduce thrombus formation. The interior surface 1208 of the conduit 202 may be substantially smooth or wrinkle free to avoid thrombus formation by way of being formed of the single piece or run of graft material (the graft component 320). The graft component 320 may form the interior surface 1208 of the conduit 202 and be everted over the first end 1202 up to the integrated collar 804 and everted over the second end 1204 up to the anchoring structure 102. The integrated collar 804 collar may be configured to connect to the pump in order to maintain laminar flow and avoid thrombus and turbulence within the conduit 202.

In certain instances, the integrated collar 804 may facilitate maintaining the lumen of the conduit 202 open during pump cycles. The connecting between the conduit 202 and the pump (not shown) may have a large amount of force during cycling of the pump, and the integrated collar 804 (which may have a greater stiffness or radial strength that the conduit 202) may resist collapse of the conduit 202 at that point. The integrated collar 804 may add stiffness and kind resistance at the pump-to-conduit interface. The integrated collar 804 may also facilitate ease of connection the pump.

In certain instances, a second graft component 1201 may be used to secure the integrated collar 804 to the cannula 100. The integrated collar 804 may include windows or openings 1010. The windows or openings 1010 may facilitate attachment between the integrated collar 804 and the conduit 202. The second graft component 1210 may be arranged about the portion of the integrated collar 804 with the windows or openings 1010 and provide coupling or adhesive attachment (e.g., using Fluorinated ethylene propylene (FEP) between the second graft component 1210 and the conduit 202.

As discussed in detail above, the cannula 100 may include a support structure 1102 that extends along the exterior surface 1206 of the cannula 100 between the integrated collar 804 and the anchoring structure 102. The support structure 1102 may include an elongate member having a substantially rectangular cross-section, or in different terms, a flat wire, that extends about a circumference of the exterior surface of the conduit 202. The support structure 1102 may provide radial strength to the conduit 202 (e.g., being biased toward an open configuration).

The support structure 1102, in certain instances, is configured to resist collapse of the conduit 202 during operation of the pump. For example, the support structure 1102 may be configured to avoid foreshortening and collapse of the conduit 202 during pump operation by being biased toward a radially expanded state to provide radial and longitudinal reinforcement to the conduit 202. The support structure 1102 may be configured to provide such reinforcement to the conduit 202 to resist collapse while also allowing for flattening and compression of the conduit 202 (e.g., using a forceps, pincers, or other tool) to allow for blocking/closing of the conduit 202 at a desired time (e.g., during connection to the pump, for example). The support structure 1102 may be self-expanding to allow for crush and re-expansion. In this regard, the support structure 1102 may also avoid kinking of the conduit 202 during implant.

The support structure 1102 may be coupled to the exterior surface 1206 of the conduit by a third graft component 1212. The support structure 1102 may keep the cannula 100 smooth along the exterior surface 1206 and the interior surface 1208. The third graft component 1212 may also be used to couple the anchoring structure 102 to the cannula 100 and cover stent portions that extend along the exterior surface 1206 of the cannula. The stent portions 430, 432 are shown covered by a graft component in FIG. 4. The third graft comment 1212 may also facilitate folding of the first anchor portion 304 and the second anchor portion 308 and allow for laying flat of the first anchor portion 304 and the second anchor portion 308 in a delivery configuration. This also provides minimal bending for loading of the first anchor portion 304 and the second anchor portion 308 in a delivery configuration. The flat wire configuration of the support structure 1102 also facilitates the smooth exterior surface 1206 and laying flat of the first anchor portion 304 and the second anchor portion 308.

In certain instances, the anchoring structure 102 may include a fourth graft component 312 that covers and/or extends between one or more open spaces 322 defined by each of the plurality of first contact features 306 and the plurality of second contact features 310. As discussed in detail above, the first anchor portion 304 and the second anchor portion 308 may be configured to fold or collapse toward the exterior surface 324 of the conduit 202 in a delivery configuration. The contact features 306, 310 may be formed of a stent structure and the graft component 320 may cover the stent structure.

As shown, a distal end portion 320 of the conduit 202 may extend distal of, or beyond the anchoring structure 102. The distal end portion 320 may define a length that is configured or otherwise selected to avoid tissue ingrowth along the conduit 202 that could otherwise obstruct the inlet of the conduit 202 (which corresponds to the distal end portion 320 as shown). In certain instances, the distal end portion 320 of the conduit 202 may have a length that is selected to avoid or is biased to avoid suctioning or obstructing the anatomy of the heart (e.g., valve leaflets). The distal end portion 320 is configured to extend into the heart without contacting other areas of the heart that could affect the heart performance. In certain instances, the distal end portion 320 of the conduit 202 may end between about 5 mm to about 10 mm beyond the second anchoring portion 308. In addition, the distance between the first and second anchoring portions 304, 308 may be between about 0 mm to 2 mm, in certain instances. In addition, the distal end portion 320 of the conduit 202 may include the first graft component 320 that includes a closed structure that avoids tissue ingrowth. The fourth graft component 312 arranged with the first and second anchoring portions 304, 308 may be an open structure configured to facilitate tissue ingrowth. The remaining portions of the first graft component 320 that extend along the interior surface 1208 may also include a closed structure that avoids tissue ingrowth and the third graft component 1212 that extends over the exterior surface 1206 of the conduit 202 (e.g., between the anchoring portion 102 and the integrated collar 804) may also include a closed structure that avoids tissue ingrowth.

The construction of the cannula 100 results in a smooth, resilient low-profile, flexible integrated device, which may facilitate a reduced risk of thrombus. The integrated graft and structural components may provide smoothness to both the interior surface 1208 and/or exterior surface 1206 of the cannula 100 while also not collapsing during pump operation (either at the first end 1202 or along the length of the conduit 202).

A biocompatible material for the graft components, discussed herein, may be used. In certain instances, the graft may include a fluoropolymer, such as a polytetrafluoroethylene (PTFE) polymer or an expanded polytetrafluoroethylene (ePTFE) polymer. In some instances, the graft may be formed of, such as, but not limited to, a polyester, a silicone, a urethane, a polyethylene terephthalate, or another biocompatible polymer, or combinations thereof. In some instances, bioresorbable or bioabsorbable materials may be used, for example a bioresorbable or bioabsorbable polymer. In some instances, the graft can include Dacron, polyolefins, carboxy methylcellulose fabrics, polyurethanes, or other woven, nonwoven, or film elastomers.

In addition, nitinol (NiTi) may be used as the material of the frame or stent (and any of the frames discussed herein), but other materials such as, but not limited to, stainless steel, L605 steel, polymers, MP35N steel, polymeric materials, Pyhnox, Elgiloy, or any other appropriate biocompatible material, and combinations thereof, can be used as the material of the frame. The super-elastic properties and softness of NiTi may enhance the conformability of the stent. In addition, NiTi can be shape-set into a desired shape. That is, NiTi can be shape-set so that the frame tends to self-expand into a desired shape when the frame is unconstrained, such as when the frame is deployed out from a delivery system.

In certain instances, the coating, as discussed in detail above, may include bio-active agents in addition to heparin or alternatively to heparin. The agents can include, but are not limited to, vasodilator, anti-coagulants, anti-platelet, anti-thrombogenic agents.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A cannula comprising:

a conduit having an exterior surface and an interior surface that includes a single piece of a first graft component arranged along the interior surface and being everted over a first end and a second end of the conduit to reduce disruption of fluid flow along the interior surface of the conduit; and a support structure including an elongate element having a rectangular cross-section, the elongate element being coupled to the exterior surface of the conduit by a second graft component and extending along a length thereof.

2. The cannula of claim 1, further including an anchoring structure arranged adjacent an end of the conduit configured to engage with tissue and anchor the conduit.

3. The cannula of claim 2, wherein the anchoring structure includes a first anchor portion having a stent portion extending along the exterior surface of the conduit to facilitate folding of the first anchor portion toward the exterior surface of the conduit in a delivery configuration, and a second anchor portion having a stent portion extending along the exterior surface of the conduit to facilitate folding of the second anchor portion toward the exterior surface of the conduit in the delivery configuration.

4. The cannula of claim 1, further comprising an integrated collar arranged at one of the first end or the second end of the conduit configured to interface with a pump device and lessen an opportunity for collapse of the conduit during operation of the pump device.

5. The cannula of claim 4, wherein the integrated collar includes a plurality of windows and a third graft component is arranged about the integrated collar at the plurality of windows to secure the integrated collar to the conduit.

6. The cannula of claim 1, wherein the conduit is configured to interface with a pump device, and the support structure is configured to resist collapse of the conduit during operation of the pump device.

7. The cannula of claim 1, wherein the interior surface of the conduit is configured to reduce thrombus formation, the interior surface of the conduit having a substantially uninterrupted surface.

8. A cannula comprising:

a conduit having an exterior surface and an interior surface, a proximal end and a distal end;

an anchoring structure attached to the conduit adjacent an end of the conduit, the anchoring structure including:

a first anchor portion having a plurality of first contact features and a first stent element extending along the exterior surface of the conduit toward the distal end of the conduit, and a second anchor portion having a plurality of second contact features and a second stent element extending along the exterior surface of the conduit toward the proximal end of the conduit, the first stent element being configured to facilitate folding of the first anchor portion toward the exterior surface of the conduit and adjacent the second stent element and the second stent element is configured to facilitate folding of the second anchor portion toward the exterior surface of the conduit and adjacent the first stent element in a delivery configuration.

9. The cannula of claim 8, wherein the plurality of first contact features and the second plurality of contact features each include a first substantially linear section extending from the exterior surface of the conduit in a first direction, a second substantially linear section extending in a second direction, different than the first direction, to an apex, a third substantially linear section extending in a third direction opposite the second direction, and a fourth substantially linear section extending toward the conduit in a fourth direction opposite the first direction.

10. The cannula of claim 9, wherein the first substantially linear section and the fourth substantially linear section are of approximately a common length.

11. The cannula of claim 9, wherein the second substantially linear section and the third substantially linear section are of approximately a common length.

12. The cannula of claim 11, wherein the length of first substantially linear section and the fourth substantially linear section is less the length of the second substantially linear section and the third substantially linear section.

13. The cannula of claim 8, wherein a space between the first anchor portion and the second first anchor portion is between about 0 mm to about 2 mm.

14. The cannula of claim 8, wherein the first anchor portion and the second anchor portion are configured to collapse toward the exterior surface of the conduit in the delivery configuration.

15. The cannula of claim 8, wherein the first anchor portion includes a first stent element arranged along the exterior surface of the conduit, and the second first anchor portion includes a second stent element arranged along the exterior surface of the conduit.

16. The cannula of claim 15, wherein the first stent element extends along the exterior surface of the conduit toward and past the second anchor portion and the second stent element extends along the exterior surface of the conduit toward and past the first anchor portion.

17. The cannula of claim 15, wherein the first stent element is looped back toward the first anchor portion and the second stent element is looped back toward the second anchor portion.

18. The cannula of claim 8, wherein each of the plurality of first contact features have a diamond shape and each of the plurality of second contact features have a diamond shape.

19. The cannula of claim 8, wherein the first anchor portion defines one or more open spaces between the plurality of first contact features, and a graft extends between the plurality of first contact features to cover the one or more open spaces.

20. The cannula of claim 8, wherein the first contact features and the second contact features are each formed of a stent structure and a graft covering at least a portion of the stent structure.

21. The cannula of claim 8, wherein the first anchor portion folds toward the exterior surface of the conduit in a first direction toward a first end of conduit and the second anchor portion folds toward the exterior surface of the conduit in a second direction toward a second end of the conduit, wherein the first end is positioned opposite the second end.

22. A cannula comprising:

a conduit having an exterior surface and an interior surface;

an anchoring structure arranged adjacent an end of the conduit configured to engage with tissue and anchor the conduit, the anchoring structure including:

- a first anchor portion having a plurality of first contact features extending longitudinally outward relative to the exterior surface of the conduit and a stent portion extending along the exterior surface of the conduit to facilitate folding of the first anchor portion toward the exterior surface of the conduit and in a first direction in a delivery configuration, and
- a second anchor portion having a plurality of second contact features extending longitudinally outward relative to the exterior surface of the conduit and a stent portion extending along the exterior surface of the conduit to facilitate folding of the second anchor portion toward the exterior surface of the conduit and in a second direction opposite the first direction in the delivery configuration.

23. The cannula of claim 22, wherein the first stent element extends along the exterior surface of the conduit toward and past the second anchor portion and the second stent element extends along the exterior surface of the conduit toward and past the first anchor portion.

24. The cannula of claim 22, wherein the first stent element is looped back toward the first anchor portion and the second stent element is looped back toward the second anchor portion.

25. The cannula of claim 22, wherein the first stent element is configured to facilitate folding of the first anchor portion toward the exterior surface of the conduit and adjacent the second stent element and the second stent element is configured to facilitate folding of the second anchor portion toward the exterior surface of the conduit and adjacent the first stent element in the delivery configuration.

26. The cannula of claim 22, wherein the plurality of first contact features and the second plurality of contact features each include a first substantially linear section extending from the exterior surface of the conduit in a first direction, a second substantially linear section extending in a second direction, different than the first direction, to an apex, a third substantially linear section extending in a third direction opposite the second direction, and a fourth substantially linear section extending toward the conduit in a fourth direction opposite the first direction.

27. The cannula of claim 22, further including a connector that is integrated to the conduit configured to facilitate attachment to a pump and reduction of thrombus formation.

* * * * *